(12) United States Patent
Hughes et al.

(10) Patent No.: US 10,405,757 B2
(45) Date of Patent: Sep. 10, 2019

(54) PATIENT MONITORING SYSTEM WITH GATEKEEPER SIGNAL

(71) Applicant: ICU Medical, Inc., San Clemente, CA (US)

(72) Inventors: Timothy John Hughes, Palo Alto, CA (US); Lina Derderian, Trabuco Canyon, CA (US)

(73) Assignee: ICU Medical, Inc., San Clemente, CA (US)

( * ) Notice: Subject to any disclaimer, the term of this patent is extended or adjusted under 35 U.S.C. 154(b) by 12 days.

(21) Appl. No.: 15/118,834

(22) PCT Filed: Feb. 24, 2015

(86) PCT No.: PCT/US2015/017377
§ 371 (c)(1),
(2) Date: Aug. 12, 2016

(87) PCT Pub. No.: WO2015/130705
PCT Pub. Date: Sep. 3, 2015

(65) Prior Publication Data
US 2017/0055848 A1 Mar. 2, 2017

Related U.S. Application Data

(60) Provisional application No. 61/944,408, filed on Feb. 25, 2014.

(51) Int. Cl.
*A61B 5/02* (2006.01)
*A61B 5/0215* (2006.01)
(Continued)

(52) U.S. Cl.
CPC ........ *A61B 5/0215* (2013.01); *A61B 5/02141* (2013.01); *A61B 2017/0023* (2013.01);
(Continued)

(58) Field of Classification Search
CPC ... A61M 2025/0003; A61B 2560/0271; A61B 2560/028; A61B 2560/0285;
(Continued)

(56) References Cited

U.S. PATENT DOCUMENTS 3,618,592 A 11/1971 Stewart
3,868,679 A 2/1975 Arneson
(Continued)

FOREIGN PATENT DOCUMENTS

JP 62-129032 6/1987
WO WO 1998/25532 6/1998
(Continued)

OTHER PUBLICATIONS

US 8,613,701 B2, 12/2013, Rao et al. (withdrawn)
(Continued)

*Primary Examiner* — Christian Jang
*Assistant Examiner* — Andrey Shostak
(74) *Attorney, Agent, or Firm* — Knobbe Martens Olson & Bear, LLP

(57) ABSTRACT

A gatekeeper electronic signal can be generated by a patient sensor and/or in an intermediate device, such as an electrical cable, that is separate from a patient's physiological information electronic signal. The gatekeeper signal can be generated to indicate to a computer monitor that the sensor and/or cable is of the type that is compatible with, and/or usable with, such computer monitor, and/or that the sensor and/or cable is properly attached to the computer monitor. The gatekeeper signal can be created by an ambient temperature sensor on, or in electrical communication with, the patient monitor, and/or the gatekeeper signal can be created by a gatekeeper electronic signal generator to simulate an ambient temperature value. The gatekeeper signal can be separate from an electronic signal or plurality of signals that (Continued)

include patient physiological information, and the gatekeeper signal may not include any patient physiological information.

8 Claims, 4 Drawing Sheets

(51) Int. Cl.
*A61B 5/021* (2006.01)
*A61B 17/00* (2006.01)
*A61M 25/00* (2006.01)

(52) U.S. Cl.
CPC ..... *A61B 2505/03* (2013.01); *A61B 2560/028* (2013.01); *A61B 2560/0252* (2013.01); *A61B 2560/0266* (2013.01); *A61B 2560/0271* (2013.01); *A61B 2560/0276* (2013.01); *A61B 2560/0285* (2013.01); *A61B 2560/0443* (2013.01); *A61B 2562/08* (2013.01); *A61B 2562/222* (2013.01); *A61B 2562/225* (2013.01); *A61B 2562/226* (2013.01); *A61B 2562/227* (2013.01); *A61M 2025/0003* (2013.01)

(58) Field of Classification Search
CPC ............ A61B 2562/226; A61B 5/0215; A61B 5/02141; A61B 2562/08; A61B 2562/227; A61B 2562/222; A61B 2562/225; A61B 2560/0266; A61B 2560/0252; A61B 2560/0276; A61B 2560/225; A61B 2017/0023; A61B 2505/03
See application file for complete search history.

(56) References Cited

U.S. PATENT DOCUMENTS

| | | |
|---|---|---|
| 4,465,075 A | 8/1984 | Swartz |
| 4,501,531 A | 2/1985 | Bilstad et al. |
| 4,550,611 A | 11/1985 | Czarnocki |
| 4,557,269 A | 12/1985 | Reynolds et al. |
| 4,581,940 A | 4/1986 | Merrick et al. |
| 4,611,601 A | 9/1986 | Bowman |
| 4,659,235 A | 4/1987 | Gilmore, Jr. et al. |
| 4,679,567 A | 7/1987 | Hanlon et al. |
| 4,683,894 A | 8/1987 | Kodama et al. |
| 4,685,469 A | 8/1987 | Keller |
| 4,817,022 A | 3/1989 | Jomod et al. |
| 4,825,876 A | 5/1989 | Beard |
| 4,883,992 A | 11/1989 | Koglin et al. |
| 4,926,674 A | 5/1990 | Fossum et al. |
| 4,950,235 A | 8/1990 | Slate et al. |
| 5,135,002 A | 8/1992 | Kirchner et al. |
| 5,269,311 A | 12/1993 | Kirchner et al. |
| 5,400,793 A | 3/1995 | Wesseling |
| 5,526,817 A | 6/1996 | Pfeiffer et al. |
| 5,579,771 A | 12/1996 | Bonnefous |
| 5,623,925 A | 4/1997 | Swenson et al. |
| 5,640,953 A | 6/1997 | Bishop et al. |
| 5,685,314 A | 11/1997 | Geheb et al. |
| 5,712,795 A | 1/1998 | Layman et al. |
| 5,713,856 A | 2/1998 | Eggers et al. |
| 5,746,698 A | 5/1998 | Bos et al. |
| 5,781,442 A | 7/1998 | Engleson et al. |
| 5,800,387 A | 9/1998 | Duffy et al. |
| 5,803,917 A | 9/1998 | Butterfield et al. |
| 5,827,223 A | 10/1998 | Butterfield et al. |
| 5,836,910 A | 11/1998 | Duffy et al. |
| 5,848,988 A | 12/1998 | Davis |
| 5,904,708 A | 5/1999 | Goedeke |
| 5,908,027 A | 6/1999 | Butterfield et al. |
| 5,941,846 A | 8/1999 | Duffy et al. |
| 5,954,641 A | 9/1999 | Kehr et al. |
| 5,957,885 A | 9/1999 | Bollish et al. |
| 5,961,487 A | 10/1999 | Davis |
| 6,045,512 A | 4/2000 | Roteliuk et al. |
| 6,050,951 A | 4/2000 | Friedman et al. |
| 6,071,244 A | 6/2000 | Band et al. |
| 6,085,752 A | 7/2000 | Kehr et al. |
| 6,102,855 A | 8/2000 | Kehr et al. |
| 6,113,543 A | 9/2000 | Bonnefous |
| 6,158,965 A | 12/2000 | Butterfield et al. |
| 6,159,151 A | 12/2000 | Bonnefous |
| 6,183,417 B1 | 2/2001 | Geheb et al. |
| 6,200,301 B1 | 3/2001 | Pfeiffer et al. |
| 6,213,972 B1 | 4/2001 | Butterfield et al. |
| 6,224,585 B1 | 5/2001 | Pfeiffer |
| 6,231,498 B1 | 5/2001 | Pfeiffer et al. |
| 6,270,252 B1 | 8/2001 | Siefert |
| 6,290,650 B1 | 9/2001 | Butterfield et al. |
| 6,315,735 B1 | 11/2001 | Joeken et al. |
| 6,348,777 B1 | 2/2002 | Brown et al. |
| 6,358,213 B1 | 3/2002 | Friedman et al. |
| 6,358,225 B1 | 3/2002 | Butterfield |
| 6,394,961 B1 | 5/2002 | Pfeiffer et al. |
| 6,416,291 B1 | 7/2002 | Butterfield et al. |
| 6,485,431 B1 | 11/2002 | Campbell |
| 6,485,481 B1 | 11/2002 | Pfeiffer |
| 6,506,163 B1 | 1/2003 | Farrell et al. |
| 6,532,381 B2 | 3/2003 | Bayer et al. |
| 6,537,214 B1 | 3/2003 | Hood et al. |
| 6,562,012 B1 | 5/2003 | Brown et al. |
| 6,575,901 B2 | 6/2003 | Stoycos et al. |
| 6,582,370 B2 | 6/2003 | Jibiki |
| 6,589,264 B1 | 7/2003 | Barbut et al. |
| 6,591,135 B2 | 7/2003 | Palmer et al. |
| 6,592,546 B1 | 7/2003 | Barbut et al. |
| 6,602,191 B2 | 8/2003 | Quy |
| 6,609,023 B1 | 8/2003 | Fischell et al. |
| 6,611,206 B2 | 8/2003 | Eshelman et al. |
| 6,645,177 B1 | 11/2003 | Shearn |
| 6,648,828 B2 | 11/2003 | Friedman et al. |
| 6,671,547 B2 | 12/2003 | Lyster et al. |
| 6,671,563 B1 | 12/2003 | Engelson et al. |
| 6,673,018 B2 | 1/2004 | Friedman |
| 6,698,921 B2 | 3/2004 | Siefert |
| 6,699,203 B2 | 3/2004 | Starr et al. |
| 6,705,992 B2 | 3/2004 | Gatzke |
| 6,731,973 B2 | 5/2004 | Voith |
| 6,731,989 B2 | 5/2004 | Engleson et al. |
| 6,736,782 B2 | 5/2004 | Pfeiffer et al. |
| 6,746,431 B2 | 6/2004 | Pfeiffer et al. |
| 6,758,822 B2 | 7/2004 | Romano |
| 6,801,802 B2 | 10/2004 | Sitzman et al. |
| 6,829,501 B2 | 12/2004 | Nielsen et al. |
| 6,840,904 B2 | 1/2005 | Goldberg |
| 6,862,472 B2 | 3/2005 | Mikula et al. |
| 6,870,475 B2 | 3/2005 | Fitch et al. |
| 6,904,306 B1 | 6/2005 | Wu et al. |
| 6,915,170 B2 | 7/2005 | Engleson et al. |
| 6,997,877 B2 | 2/2006 | Band et al. |
| 7,011,672 B2 | 3/2006 | Barbut et al. |
| 7,022,322 B2 | 4/2006 | Koll et al. |
| 7,054,679 B2 | 5/2006 | Hirsh |
| 7,074,205 B1 | 7/2006 | Duffy et al. |
| 7,092,751 B2 | 8/2006 | Erkkila |
| 7,209,780 B2 | 4/2007 | Pfeiffer et al. |
| 7,220,230 B2 | 5/2007 | Roteliuk et al. |
| D552,741 S | 10/2007 | Zhou et al. |
| 7,280,864 B2 | 10/2007 | Jenkins |
| 7,297,129 B2 | 11/2007 | Kinouchi et al. |
| 7,306,575 B2 | 12/2007 | Barbut et al. |
| 7,314,449 B2 | 1/2008 | Pfeiffer et al. |
| 7,319,894 B2 | 1/2008 | Higgins |
| 7,344,551 B2 | 3/2008 | Barbut et al. |
| 7,384,410 B2 | 6/2008 | Eggers et al. |
| 7,390,302 B2 | 6/2008 | Friedman et al. |
| 7,407,486 B2 | 8/2008 | Huiku et al. |
| 7,422,562 B2 | 9/2008 | Hatib et al. |
| 7,452,333 B2 | 11/2008 | Roteliuk |
| 7,465,273 B2 | 12/2008 | Friedman |
| 7,468,035 B2 | 12/2008 | Bonan et al. |

(56) References Cited

U.S. PATENT DOCUMENTS

| | | |
|---|---|---|
| 7,468,038 B2 | 12/2008 | Ye et al. |
| 7,507,208 B2 | 3/2009 | Bennett et al. |
| 7,542,795 B2 | 6/2009 | Brodnick |
| 7,553,291 B2 | 6/2009 | Duffy et al. |
| 7,559,896 B2 | 7/2009 | Torp |
| 7,569,015 B2 | 8/2009 | Donaldson et al. |
| 7,572,223 B2 | 8/2009 | Donaldson |
| 7,572,230 B2 | 8/2009 | Neumann et al. |
| 7,588,542 B2 | 9/2009 | Pfeiffer et al. |
| 7,590,449 B2 | 9/2009 | Mann et al. |
| 7,594,892 B2 | 9/2009 | Cen et al. |
| 7,604,602 B2 | 10/2009 | Roteliuk et al. |
| 7,608,060 B2 | 10/2009 | Gillepsie, Jr. et al. |
| 7,611,467 B2 | 11/2009 | Zhang |
| 7,650,291 B2 | 1/2010 | Rosenfeld et al. |
| 7,651,466 B2 | 1/2010 | Hatib et al. |
| 7,666,151 B2 | 2/2010 | Sullivan et al. |
| 7,678,059 B2 | 3/2010 | Friedman et al. |
| 7,695,512 B2 | 4/2010 | Lashinski et al. |
| 7,704,209 B2 | 4/2010 | Bennett et al. |
| 7,766,863 B2 | 8/2010 | Giliepsie, Jr. et al. |
| 7,775,987 B2 | 8/2010 | Hersh et al. |
| 7,783,339 B2 | 8/2010 | Lee et al. |
| 7,785,263 B2 | 8/2010 | Roteliuk et al. |
| 7,803,122 B2 | 9/2010 | Pfeiffer et al. |
| 7,805,181 B2 | 9/2010 | Breeuwer |
| 7,815,576 B2 | 10/2010 | Wellnhofer |
| 7,815,578 B2 | 10/2010 | Cohen et al. |
| 7,837,628 B2 | 11/2010 | Secora et al. |
| 7,850,617 B2 | 12/2010 | Goedje et al. |
| 7,873,416 B2 | 1/2011 | Guo et al. |
| D632,698 S | 2/2011 | Judy et al. |
| D632,699 S | 2/2011 | Judy et al. |
| 7,927,269 B2 | 4/2011 | Ten Eyck et al. |
| 7,935,062 B2 | 5/2011 | Karamanoglu et al. |
| 7,966,678 B2 | 6/2011 | Ten Eyck et al. |
| 7,967,749 B2 | 6/2011 | Hutchinson et al. |
| 7,967,757 B2 | 6/2011 | Roteliuk |
| 7,979,111 B2 | 7/2011 | Acquista |
| 7,991,625 B2 | 8/2011 | Rosenfeld et al. |
| 7,993,274 B2 | 8/2011 | Pruvot et al. |
| 8,000,937 B2 | 8/2011 | Zeng et al. |
| 8,016,766 B2 | 9/2011 | Goedje et al. |
| 8,025,674 B2 | 9/2011 | Barbut et al. |
| RE42,803 E | 10/2011 | Lipson et al. |
| D649,556 S | 11/2011 | Judy et al. |
| 8,050,748 B2 | 11/2011 | Ali et al. |
| 8,060,203 B2 | 11/2011 | JÄRverud et al. |
| 8,070,677 B2 | 12/2011 | Ali |
| D652,051 S | 1/2012 | Judy et al. |
| D652,052 S | 1/2012 | Judy et al. |
| 8,096,947 B2 | 1/2012 | Salgo et al. |
| 8,115,101 B2 | 2/2012 | Balji et al. |
| 8,125,484 B2 | 2/2012 | Gering |
| 8,137,273 B2 | 3/2012 | Everett et al. |
| 8,170,887 B2 | 5/2012 | Rosenfeld et al. |
| 8,175,895 B2 | 5/2012 | Rosenfeld et al. |
| 8,182,429 B2 | 5/2012 | Mason |
| 8,211,030 B2 | 7/2012 | Donehoo et al. |
| 8,233,272 B2 | 7/2012 | Fidacaro et al. |
| 8,235,938 B2 | 8/2012 | Eggers et al. |
| 8,246,546 B2 | 8/2012 | Huiku |
| 8,257,273 B2 | 9/2012 | Pfeiffer et al. |
| 8,266,349 B2 | 9/2012 | Eaton et al. |
| 8,279,586 B2 | 10/2012 | Fidacaro et al. |
| 8,282,567 B2 | 10/2012 | Kolluri et al. |
| 8,285,360 B2 | 10/2012 | Kabasawa |
| 8,315,682 B2 | 11/2012 | Such et al. |
| 8,326,649 B2 | 12/2012 | Rosenfeld |
| 8,343,058 B2 | 1/2013 | Pfeiffer et al. |
| 8,343,062 B2 | 1/2013 | Fortin et al. |
| 8,344,847 B2 | 1/2013 | Moberg et al. |
| 8,396,537 B2 | 3/2013 | Balji et al. |
| 8,401,874 B2 | 3/2013 | Rosenfeld |
| 8,465,424 B2 | 6/2013 | Aggarwal |
| 8,465,435 B2 | 6/2013 | Van Goudoever et al. |
| 8,469,887 B2 | 6/2013 | Haider |
| 8,471,697 B2 | 6/2013 | Judy et al. |
| 8,483,789 B2 | 7/2013 | Higgins |
| 8,484,393 B2 | 7/2013 | Eaton et al. |
| 8,515,531 B2 | 8/2013 | Costa Ribalta et al. |
| 8,517,939 B2 | 8/2013 | Parnagian |
| 8,521,556 B2 | 8/2013 | Chbat et al. |
| 8,548,577 B2 | 10/2013 | Muhlsteff et al. |
| 8,562,526 B2 | 10/2013 | Heneghan et al. |
| 8,566,738 B2 | 10/2013 | Van Vlimmeren et al. |
| 8,568,327 B2 | 10/2013 | O'Brien |
| 8,574,156 B2 | 11/2013 | Uutela et al. |
| 8,574,157 B2 | 11/2013 | Hoctor et al. |
| 8,602,985 B2 | 12/2013 | Ali |
| 8,622,913 B2 | 1/2014 | Dentinger et al. |
| 8,639,521 B2 | 1/2014 | Eggers et al. |
| 8,641,757 B2 | 2/2014 | Pintor et al. |
| 8,645,154 B2 | 2/2014 | Eggers et al. |
| 8,649,586 B2 | 2/2014 | Wang et al. |
| 8,665,096 B2 | 3/2014 | Rantala et al. |
| 8,690,786 B2 | 4/2014 | Hersh et al. |
| 8,696,632 B2 | 4/2014 | Gillepsie, Jr. et al. |
| 8,715,193 B2 | 5/2014 | Takala et al. |
| 8,721,543 B2 | 5/2014 | Saffarian |
| 8,721,556 B2 | 5/2014 | Roteliuk |
| 8,730,243 B2 | 5/2014 | Wenholz et al. |
| 8,734,339 B2 | 5/2014 | Rao et al. |
| 8,737,048 B2 | 5/2014 | Fidacaro et al. |
| 8,737,971 B2 | 5/2014 | van Rooyen et al. |
| 8,740,807 B2 | 6/2014 | Banet et al. |
| 8,744,875 B2 | 6/2014 | Eaton et al. |
| 8,761,851 B2 | 6/2014 | Benni et al. |
| 8,771,197 B2 | 7/2014 | Hatib et al. |
| 8,771,198 B2 | 7/2014 | Kumar et al. |
| 8,773,259 B2 | 7/2014 | Judy et al. |
| 8,797,714 B2 | 8/2014 | Balji et al. |
| 8,805,019 B2 | 8/2014 | Jeanne et al. |
| 8,808,191 B2 | 8/2014 | Hirsh |
| 8,836,514 B2 | 9/2014 | Rantala |
| 8,840,636 B2 | 9/2014 | Barbut et al. |
| 8,852,094 B2 | 10/2014 | Al-Ali et al. |
| 8,878,677 B2 | 11/2014 | Nielsen et al. |
| 8,882,666 B1 | 11/2014 | Goldberg et al. |
| 8,888,738 B2 | 11/2014 | Gillepsie, Jr. et al. |
| 8,905,939 B2 | 12/2014 | Hatib et al. |
| 8,911,377 B2 | 12/2014 | Al-Ali |
| 8,922,330 B2 | 12/2014 | Moberg et al. |
| 8,923,918 B2 | 12/2014 | Kreger et al. |
| 8,992,431 B2 | 3/2015 | Merilainen |
| 9,024,781 B2 | 5/2015 | Zhang et al. |
| 9,047,648 B1 | 6/2015 | Lekutai et al. |
| 9,070,184 B2 | 6/2015 | Wang et al. |
| 9,101,264 B2 | 8/2015 | Acquista |
| 9,101,335 B2 | 8/2015 | Coffeng |
| 9,125,630 B2 | 9/2015 | Menzel |
| 9,149,188 B2 | 10/2015 | Eng et al. |
| 9,152,268 B2 | 10/2015 | Li et al. |
| 9,167,968 B2 | 10/2015 | Saeed et al. |
| 9,167,973 B2 | 10/2015 | Steiner et al. |
| 9,189,941 B2 | 11/2015 | Eschelman et al. |
| 9,196,046 B2 | 11/2015 | Meyer |
| 9,198,620 B2 | 12/2015 | Balji et al. |
| 9,204,857 B2 | 12/2015 | Dentinger |
| 9,220,421 B2 | 12/2015 | Woehrle |
| 9,254,104 B2 | 2/2016 | Judy et al. |
| 9,259,187 B2 | 2/2016 | Peyton |
| 9,300,356 B2 * | 3/2016 | Winward ............ A61B 5/0215 |
| 9,307,913 B2 | 4/2016 | O'Brien et al. |
| 9,345,641 B2 | 5/2016 | Krause et al. |
| 9,351,640 B2 | 5/2016 | Tran |
| 9,364,153 B2 | 6/2016 | Merritt et al. |
| 9,393,384 B1 | 7/2016 | Kapur et al. |
| 9,433,348 B2 | 9/2016 | Eshelman et al. |
| 9,433,386 B2 | 9/2016 | Mestha et al. |
| 9,445,764 B2 | 9/2016 | Gross et al. |
| 9,460,596 B1 | 10/2016 | Moses |
| 9,462,955 B2 | 10/2016 | Zhou et al. |
| 9,554,740 B2 | 1/2017 | Saeed et al. |

(56) References Cited

U.S. PATENT DOCUMENTS

| | | | |
|---|---|---|---|
| 9,554,756 B2 | 1/2017 | Menzel | |
| 9,607,495 B2 | 3/2017 | Tivig et al. | |
| 9,610,060 B2 | 4/2017 | Jaeschke et al. | |
| 9,659,365 B2 | 5/2017 | Groth et al. | |
| 2002/0014951 A1 | 2/2002 | Kramer et al. | |
| 2005/0020887 A1 | 1/2005 | Goldberg | |
| 2005/0197585 A1 | 9/2005 | Brockway et al. | |
| 2006/0009699 A1* | 1/2006 | Roteliuk | A61B 5/0215 600/486 |
| 2006/0281980 A1 | 12/2006 | Randlov et al. | |
| 2007/0002791 A1 | 1/2007 | Kasprzyk et al. | |
| 2007/0282208 A1 | 12/2007 | Jacobs et al. | |
| 2007/0287924 A1* | 12/2007 | Glocker | A61B 5/0002 600/493 |
| 2008/0045814 A1 | 2/2008 | Busch | |
| 2008/0058614 A1 | 3/2008 | Banet et al. | |
| 2008/0108884 A1 | 5/2008 | Kiani et al. | |
| 2008/0154100 A1 | 6/2008 | Thalmeier et al. | |
| 2008/0214903 A1 | 9/2008 | Orbach | |
| 2008/0214904 A1 | 9/2008 | Saeed et al. | |
| 2008/0221461 A1 | 9/2008 | Zhou et al. | |
| 2008/0235058 A1 | 9/2008 | Friedman et al. | |
| 2008/0255432 A1 | 10/2008 | Nielsen et al. | |
| 2008/0288180 A1* | 11/2008 | Hayter | A61B 5/0008 702/23 |
| 2009/0005703 A1 | 1/2009 | Fasciano | |
| 2009/0216132 A1 | 8/2009 | Orbach | |
| 2010/0099991 A1 | 4/2010 | Snyder | |
| 2010/0168596 A1 | 7/2010 | Jaeschke et al. | |
| 2010/0241013 A1 | 9/2010 | Hatib | |
| 2010/0259395 A1 | 10/2010 | Nuthi | |
| 2010/0261982 A1 | 10/2010 | Noury et al. | |
| 2010/0312115 A1 | 12/2010 | Dentinger | |
| 2010/0331708 A1 | 12/2010 | Hatib | |
| 2011/0009714 A1 | 1/2011 | Zong | |
| 2011/0029248 A1 | 2/2011 | Saeed et al. | |
| 2011/0060234 A1 | 3/2011 | Zhou et al. | |
| 2011/0208066 A1 | 8/2011 | Gnadinger | |
| 2011/0263992 A1 | 10/2011 | Guelen et al. | |
| 2011/0263994 A1 | 10/2011 | Burns et al. | |
| 2011/0270069 A1 | 11/2011 | Acquista | |
| 2011/0295085 A1 | 12/2011 | Goldberg | |
| 2011/0316704 A1 | 12/2011 | Nielsen et al. | |
| 2012/0078665 A1 | 3/2012 | Johnson et al. | |
| 2012/0089034 A1 | 4/2012 | Woehrle | |
| 2012/0116194 A1 | 5/2012 | Gross et al. | |
| 2012/0116218 A1 | 5/2012 | Martin et al. | |
| 2012/0123279 A1 | 5/2012 | Brueser et al. | |
| 2012/0179017 A1* | 7/2012 | Satou | A61B 5/14532 600/365 |
| 2012/0191467 A1 | 7/2012 | LaPlante et al. | |
| 2012/0197146 A1 | 8/2012 | Tan et al. | |
| 2012/0203076 A1 | 9/2012 | Fatta et al. | |
| 2012/0253156 A1 | 10/2012 | Muhlsteff | |
| 2012/0277673 A1 | 11/2012 | Levin et al. | |
| 2012/0296177 A1 | 11/2012 | Von Arx et al. | |
| 2013/0006126 A1 | 1/2013 | Band et al. | |
| 2013/0013331 A1 | 1/2013 | Horseman | |
| 2013/0046197 A1 | 2/2013 | Dlugos, Jr. et al. | |
| 2013/0053655 A1 | 2/2013 | Castellanos | |
| 2013/0085357 A1 | 4/2013 | Huber et al. | |
| 2013/0090566 A1 | 4/2013 | Muhlsteff et al. | |
| 2013/0109927 A1 | 5/2013 | Menzel | |
| 2013/0109928 A1 | 5/2013 | Menzel | |
| 2013/0109929 A1 | 5/2013 | Menzel | |
| 2013/0204104 A1 | 8/2013 | Michard et al. | |
| 2013/0245463 A1 | 9/2013 | Stuebe et al. | |
| 2013/0263855 A1 | 10/2013 | Tivig et al. | |
| 2014/0018650 A1 | 1/2014 | Lord et al. | |
| 2014/0066765 A1 | 3/2014 | Fan et al. | |
| 2014/0073883 A1 | 3/2014 | Rao et al. | |
| 2014/0074179 A1* | 3/2014 | Heldman | A61B 5/1101 607/45 |
| 2014/0077967 A1 | 3/2014 | Alvarez Osuna et al. | |
| 2014/0081089 A1 | 3/2014 | O'Neill | |
| 2014/0148702 A1 | 5/2014 | Chen | |
| 2014/0163362 A1 | 6/2014 | Pahlevan et al. | |
| 2014/0187941 A1 | 7/2014 | Shusterman | |
| 2014/0206964 A1 | 7/2014 | Saffarian | |
| 2014/0235963 A1 | 8/2014 | Edwards et al. | |
| 2014/0236249 A1 | 8/2014 | Rao et al. | |
| 2014/0257058 A1 | 9/2014 | Clarysse et al. | |
| 2014/0275849 A1 | 9/2014 | Acquista | |
| 2015/0097701 A1 | 4/2015 | Al-Ali et al. | |
| 2015/0155912 A1* | 6/2015 | Winward | A61B 5/0215 375/257 |
| 2015/0220696 A1 | 8/2015 | Lekutai et al. | |
| 2015/0306313 A1 | 10/2015 | Baykal | |
| 2015/0313505 A1 | 11/2015 | Acquista | |
| 2016/0081562 A1 | 3/2016 | Lachhman | |
| 2016/0125142 A1 | 5/2016 | Awad | |
| 2016/0203288 A1 | 7/2016 | Meng et al. | |
| 2016/0213924 A1 | 7/2016 | Coleman et al. | |
| 2016/0278869 A1 | 9/2016 | Grunwald | |
| 2018/0228386 A1 | 8/2018 | McCall et al. | |

FOREIGN PATENT DOCUMENTS

| | | | |
|---|---|---|---|
| WO | WO 2006/033812 | 3/2006 | |
| WO | WO 2006/083933 | 8/2006 | |
| WO | WO 2013088314 | 6/2013 | |
| WO | WO 2013158314 A2 * | 10/2013 | A61B 5/0215 |
| WO | WO 2013171620 | 11/2013 | |
| WO | WO 2014020484 | 2/2014 | |
| WO | WO 2015/130705 | 2/2015 | |
| WO | WO 2017/070120 | 4/2017 | |

OTHER PUBLICATIONS

U.S. Appl. No. 14/630,399, filed Feb. 24, 2015, Hughes.
International Search Report and Written Opinion for International Application No. PCT/US2015/017377, dated Jun. 3, 2015 in 10 pages.
International Preliminary Report on Patentability, for International Application No. PCT/US2015/017377, dated Sep. 9, 2016 in 6 pages.
European Extended Search Report, re EP Application No. 15755523.6, dated Sep. 28, 2017.
Anliker et al., "AMON: A Wearable Multiparameter Medical Monitoring and Alert System," IEEE Transaction on Information Technology in Biomedicine, Jan. 2005.
Philips M80001A and M80002A Data Sheet, "IntelliVue Patient Monitor MP20/MP20 Junior/MP30," 2004.

* cited by examiner

PATIENT MONITORING SYSTEM WITH GATEKEEPER SIGNAL

RELATED APPLICATIONS

This application is a U.S. National Phase of PCT/US2015/017377, which claims priority to U.S. Provisional Patent Application No. 61/944,408, filed on Feb. 25, 2014, and entitled, "Patient Monitoring System with Gatekeeper Signal," the entire contents of which are hereby incorporated by reference herein and made part of this specification for all that it discloses.

BACKGROUND

Field

Certain embodiments disclosed herein relate generally to monitoring physiological parameters of a patient, and specifically to verifying that a proper sensor is in communication with a physiological monitoring system.

Description of the Related Art

In many healthcare settings, especially in the care of seriously afflicted cardiac patients, it is desirable or necessary for a healthcare practitioner to be able to obtain generally continuous information about a patient's physiology, such as a patient's cardiac performance or a patient's blood characteristics. Electronic physiological monitoring systems can include a tubular catheter inserted into a patient's blood vessel, a sensor in fluid communication with the catheter, and a computer monitor in electrical communication with the sensor. The computer monitor is typically positioned at or near a patient's bedside and typically includes a computer processor and a display of data regarding the patient's cardiac performance.

The sensor may be a disposable component, used in treating a particular patient and then discarded and replaced with a new sensor. A variety of different types of sensors are made by different sources and purchased by healthcare facilities for different physiological monitoring systems. Several of these different types of sensors may be available in a particular healthcare setting. In addition, some sensors may be connected to the monitoring systems by one or more intermediate devices, such as one or more cables, that may be disposable or non-disposable. Some sensors and/or intermediate cables may not be validated for, or compatible with, or safe for use with, a particular physiological monitoring system. Such sensors and/or cables, if somehow connected to or placed in electrical communication with a particular physiological monitoring system, might cause damage to the monitoring system or yield false readings about a patient's current physiological condition. Moreover, even if a proper sensor and/or cable is intended to be used, but the electrical connection between the sensor and/or cable and the computer monitor is not properly connected, such as if the electrical connector is not fully inserted or includes a bent or damaged electrical contact, then an incomplete or faulty data signal may be transmitted from the sensor to the computer monitor.

SUMMARY

In some embodiments, a gatekeeper electronic signal can be generated remote from the patient monitor. In some embodiments, the gatekeeper electronic signal can be generated by a patient sensor and/or in an intermediate device, such as an electrical cable, that is separate from a patient's physiological information electronic signal. The gatekeeper signal can be generated to indicate to a computer monitor that the sensor and/or cable is of the type that is compatible with, and/or usable with, such computer monitor, and/or that the sensor and/or cable is properly attached to the computer monitor. In some embodiments, the gatekeeper signal can be created by an ambient temperature sensor on, or in electrical communication with, the patient monitor, and/or the gatekeeper signal can be created by a gatekeeper electronic signal generator to simulate an ambient temperature value. The gatekeeper signal can be separate from an electronic signal or plurality of signals that include patient physiological information, and the gatekeeper signal may not include any patient physiological information. In some embodiments, the gatekeeper signal is not configured to be used to process or evaluate any electronic signals to obtain or analyze patient physiological information.

DETAILED DESCRIPTION

Figure 1:
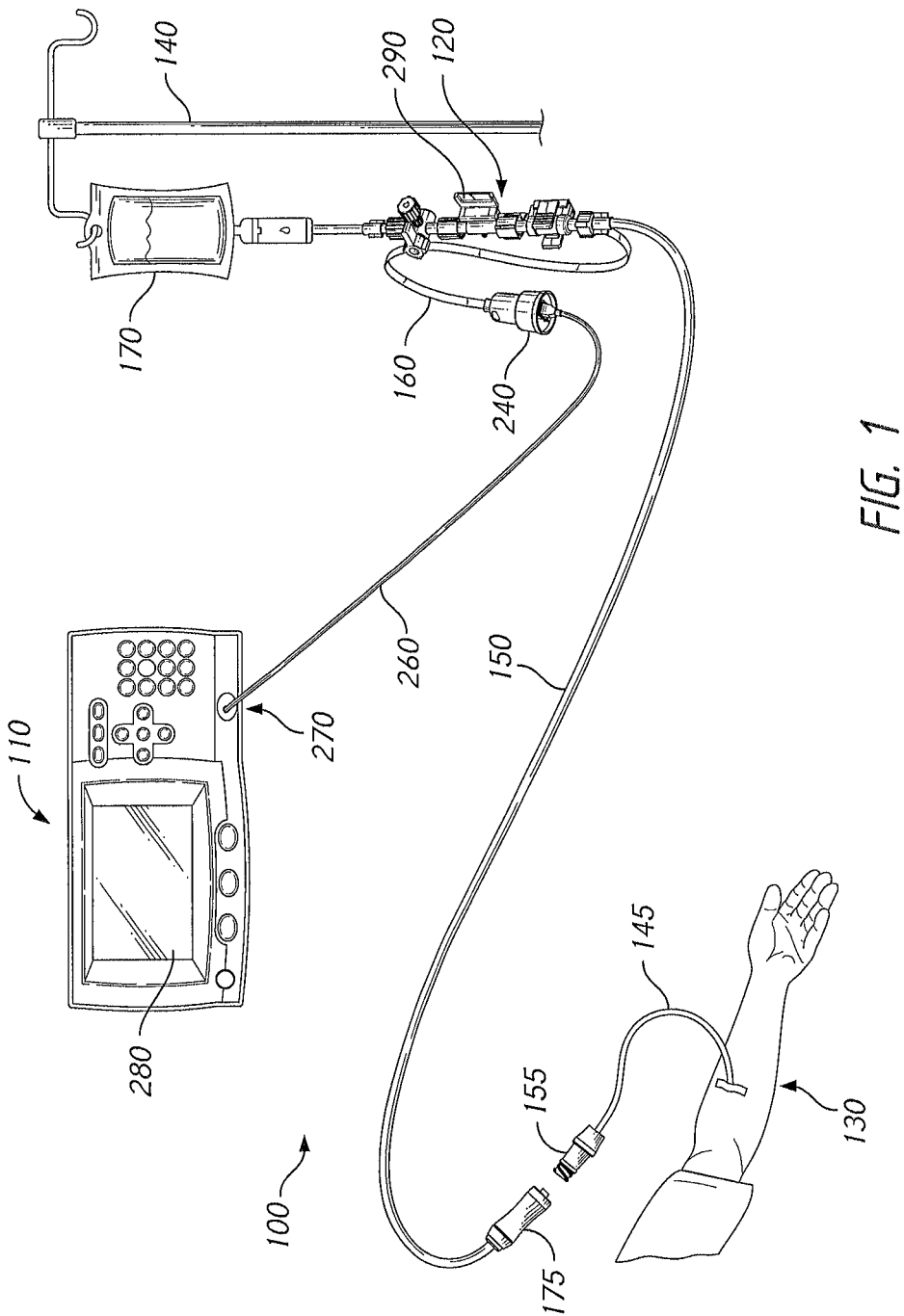
FIG. 1 illustrates an example of a critical-care patient monitoring system.

As illustrated in the example of FIG. 1, in some embodiments, a critical-care patient monitoring system 100 can include a computer monitor 110 placed in electrical communication with a patient sensor 120, such as a cardiac-monitoring sensor and/or a blood parameter sensor, which in turn is placed in fluid communication with a blood vessel of a patient 130, such as by way of a catheter 150. Though shown as an integrated unit, the computer monitor 110 may include one or more separable components; for example, the visual display, with or without embedded processing capabilities, may be releasably attached to the base computer monitor. As a patient's heart beats, a pressure wave is transmitted through the patient's interconnected system of blood vessels (veins and arteries). The pressure wave provides information about the patient's cardiac performance, which can be electrically transmitted from the patient sensor 120 to the computer monitor 110, such as by way of a wired connection 160 or a wireless connection. The information about the patient's cardiac performance can be derived or calculated through a mathematical analysis performed by the computer monitor 110 of the shape of the pressure wave, and/or the ways in which the pressure wave changes over time, etc. As shown, the patient sensor 120 can be positioned on a suitable holding structure 140, such as a pole stand or other holder, and the patient sensor can be in fluid communication with a liquid source 170.

Figure 2:
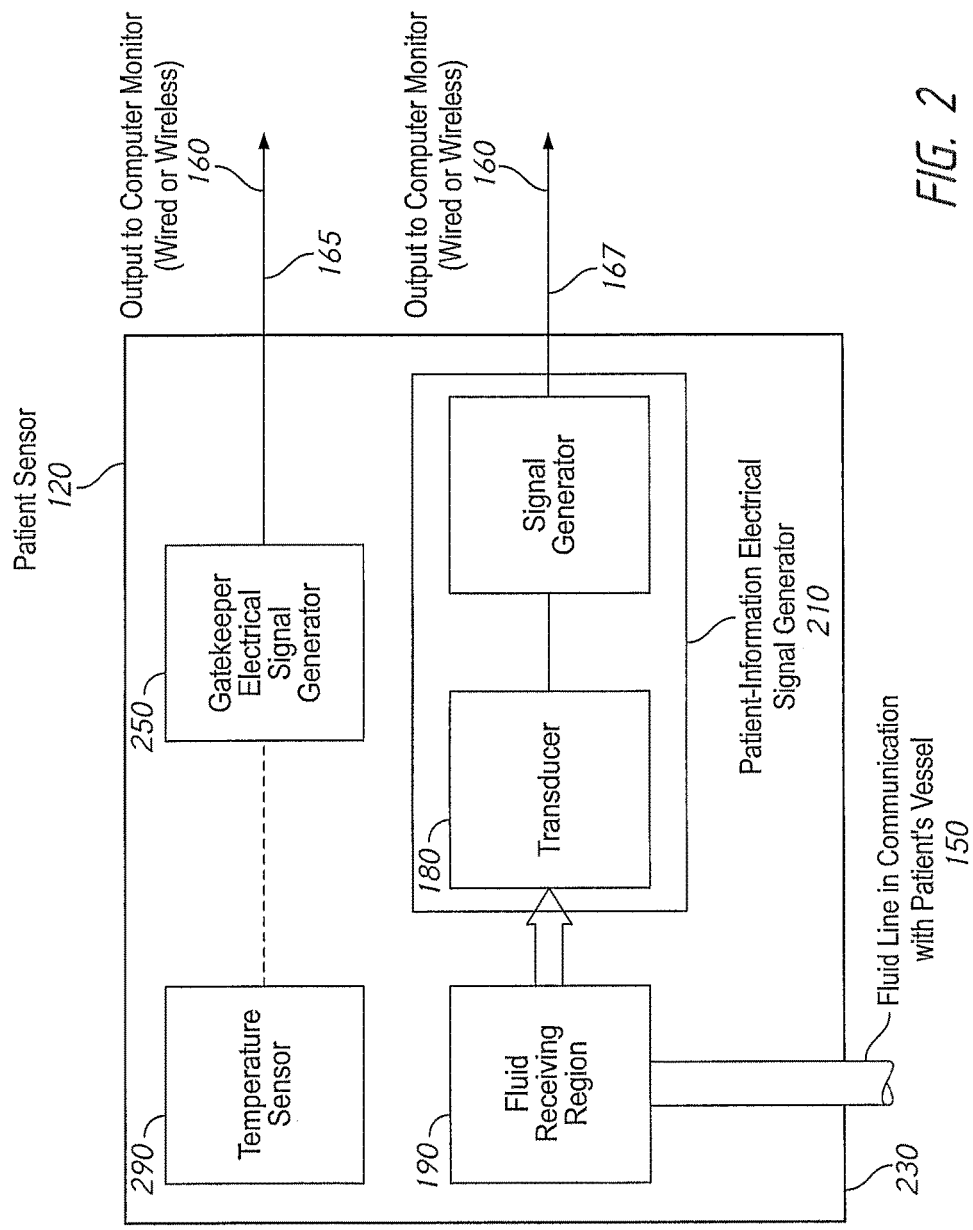
FIG. 2 illustrates an example of a schematic representation of a patient sensor that is configured to generate a gatekeeper electrical signal.
Figure 3:
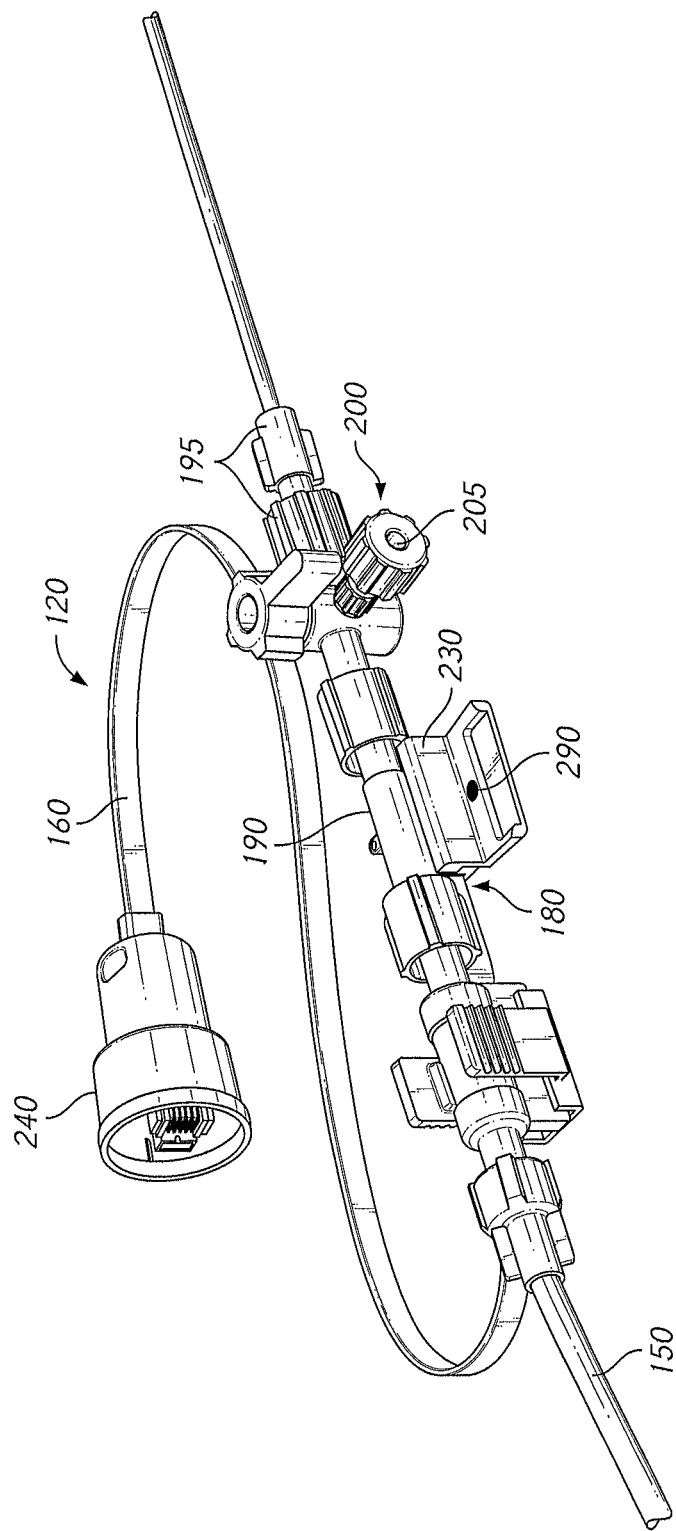
FIG. 3 illustrates an example of a patient sensor with an ambient temperature sensor.

As shown in FIGS. 2 and 3, in some embodiments, a patient sensor 120 such as a cardiac monitoring sensor can comprise a transducer 180 that is configured to transform mechanical motion into electrical energy, such as a pressure sensor that produces an electrical signal that changes over time in response to changes in fluid pressure. The patient sensor 120 can comprise a fluid-receiving region 190, such as a fluid channel, that is in communication with the transducer. The fluid channel can form part of, or be attached to, or otherwise be positioned in fluid communication with, the medical catheter 150 or other tubing or device in fluid communication with a patient's vessel. In some embodiments, the fluid-receiving region 190 is a liquid-receiving region that is configured to receive one or more liquids such as blood, water, saline, or another medical fluid. A distal end of the medical catheter can be inserted into a patient's blood vessel, in contact with the patient's blood, in a conventional manner.

The medical catheter 150 can contain a column of biocompatible fluid, such as saline and/or blood, that interfaces with the blood flowing inside of a patient's blood vessel (e.g., a vein or an artery). The column of fluid can be provided by a liquid source 170, such as an IV bag, that is pressurized or that is gravity-fed into the patient sensor 120, which can be disposed in fluid communication with the patient sensor 120 by way of one or more fluid connectors 195. A suitable valve, such as a stopcock 200 can provide a controllable connection between the liquid source 170 and the patient sensor 120. The stopcock 200 can permit fluid to flow from the liquid source 170, to the fluid-sensing region 190, and/or to or from a side port 205. As the pressure wave from the patient's beating heart is transmitted through the patient's blood vessel, the wave is communicated through fluid interaction with the blood into the column of fluid inside the medical catheter 150, and then to the fluid channel 190 at or near the transducer, where the fluid pressure wave can be converted into a cardiac monitoring electrical signal and transmitted by an electrical wire 160 or wirelessly to the computer monitor 110. The computer monitor 110 can be programmed to analyze the cardiac monitoring electrical signal to provide physiological information about the patient, such as cardiac performance information (e.g., pulse rate, blood pressure such as systolic pressure and/or diastolic pressure, and/or cardiac output, etc.).

In addition to, or instead of, providing cardiac performance information, a blood parameter sensor can be provided with a medical catheter configured to convey information about one or more blood parameters, such as one or more of: a blood gas level (e.g., oxygen and/or carbon dioxide, etc.), a pH level, a hemoglobin level, a hematocrit level, a glucose level, and/or a blood temperature, etc. In some embodiments, one or more blood parameters can be determined by measuring characteristics of light waves that are transmitted into and/or reflected from the blood or another substance in communication with the blood, such as through a system of one or more fiber optic light-transmitting and/or light-receiving cables. In some embodiments, one or more blood parameters can be determined by placing one or more sensors in close communication with the blood, such as a temperature-sensing thermistor suspended in the blood or positioned near the blood.

The patient sensor 120, whether a cardiac-monitoring sensor and/or a blood-parameter sensor, or some other form of patient sensor, can be structured, positioned, and/or oriented in a variety of different ways. The patient sensor 120 can comprise a patient-information electrical signal generator 210. In some embodiments, a physiological sensing device such as a cardiac monitoring sensor and/or a blood parameter sensor can form part of the patient-information electrical signal generator or can be in electrical communication with the patient-information electrical signal generator.

In some embodiments, the patient sensor 120 comprises a housing 230 with one or more transducers 180 or receivers positioned on or in or near the housing 120, in combination with a medical catheter 150 and one or more electrical wires 160 and/or one or more electrical connectors 240. The patient sensor 120, including the physiological sensing device or transducer 180, the patient-information electrical signal generator 210, the gatekeeper electrical signal generator 250, the medical catheter 150, the electrical wires 160, and/or the electrical connectors 240, can be a disposable unit. A patient-information electrical signal can be produced by the patient-information electrical signal generator of the patient sensor from the patient information or data obtained by one or more sensors regarding the physiological characteristics, conditions, or status of a patient. The patient's physiological information can be conveyed to or toward the computer monitor 110 of the critical-care patient monitoring system 100 by way of a patient-information electrical signal through the one or more electrical wires 160, 260 and/or one or more electrical connectors 240. In some embodiments, the patient's physiological information can be conveyed to or toward the computer monitor 110 of the critical-care patient monitoring system 100 by way of a patient-information electrical signal that is transmitted wirelessly.

In some embodiments, a non-disposable electrical cable 260 can be used to convey the patient-information electrical signal and the gatekeeper electrical signal from the electrical wires 160 in the patient sensor 120 to the computer monitor 110. In some embodiments, a gatekeeper signal-generating device 250 can be in electrical communication with such a cable or another intermediate device, or can be integrated into or embedded in such a cable or another intermediate device, instead of or in addition to being in electrical communication with or integrated into or embedded in a disposable patient sensor 120. In some healthcare settings, the distance between the transducer portion 180 of the patient sensor 120 and the computer monitor 110 can be significant, such as when the transducer 180 is positioned on a pole stand 140 or in some other location relatively close to the entry point of the medical catheter into the patient's body (such as into the patient's arm 130 or some other location) and the computer monitor 110 is located on a stand in a hospital room several feet away from the entry point, A fluid 145 catheter attached to the patient can be connected to the fluid line 150 from the sensor 120 by way of a pair of fluid connectors, such as corresponding male and female fluid connectors 155, 175.

Since the electrical wiring may be draped down from the transducer 180, across the floor, and back up to the computer monitor 110 (to avoid creating horizontal wire barriers to persons walking around the patient's vicinity), the length of electrical wiring 160, 260 between the transducer 180 and the computer monitor 110 may be in the range of about 6 feet or so (2 meters). If all of this wiring 160,260 were part of the disposable patient sensor 120, it would dramatically increase the manufacturing cost and unit price of the disposable patient sensor 120, which would be unnecessary because much of the wiring does not routinely come into contaminating contact with a patient, and need not be sterile, but is instead positioned on the floor or near the computer monitor, and can therefore be used with multiple patients. In some embodiments, the electrical connection with the patient sensor 120 is achieved by attaching an electrical connection portion 240 of the patient sensor 120 to a proximal electrical connection portion of the non-disposable cable, and then attaching a distal connection portion of the non-disposable cable 270 to an electrical connection portion of the computer monitor.

The electrical information can be conveyed in some embodiments wirelessly, such as by way of an electromagnetic short-range signal, such as over a WI-FI® network or by way of a BLUETOOTH® signal or a ZIGBEE® signal, or by some other wireless protocol that is acceptable or utilized in a healthcare setting. Any description or illustration in this specification of an electrical wire 160, 250, or electrical connection 140 can be accomplished in a wireless manner and such descriptions or illustrations of wires or electrical connections should be understood to also refer to and encompass wireless connections. For example, any description or illustration of a patient-information electrical signal and/or a gatekeeper electrical signal being conveyed over a wired connection should be understood to also refer to and encompass a suitable wireless connection.

To help verify that a proper patient sensor 120 is attached to the computer monitor 110 and/or that a proper secondary cable 270 is attached to the computer monitor 110 and/or to ensure that the electrical connection between the sensor 120 and the computer monitor 110 is properly established, a gatekeeper electrical signal can be transmitted to the monitor 110. In some embodiments, the signal is generated by a component permanently coupled to the sensor device. In some embodiments, the signal is generated at least in part by the non-disposable cable configured to place the sensor in electrical communication with the computer monitor. In some embodiments, the signal is generated by a combination of both the components permanently coupled to the sensor device and the non-disposable cable configured to place the device in electrical communication with the computer monitor. In some embodiments, the receipt of the gatekeeper electrical signal by the computer monitor is a required condition for the computer monitor 110 to function and/or for the computer monitor 110 to display patient information on a display screen 280. In some embodiments, the monitor 110 will only calculate and display physiological information about the patient after the monitor 110 receives the gatekeeper electrical signal and/or only for so long as the gatekeeper electrical signal continues to be transmitted to the monitor (continuously or within an allowable time interval). In some embodiments, if the gatekeeper electrical signal is not received by the computer monitor as expected, an error message will be conveyed on the display screen or in some other manner. The error message can indicate that no sensor is connected, that an improper sensor is connected to the computer monitor, and/or that the user should check an electrical attachment with the computer monitor, etc.

The gatekeeper electrical signal can be generated by a signal generator in a variety of different ways and in a variety of different locations. As shown in the example of FIG. 2, in some embodiments, the signal generator for producing the gatekeeper electrical signal is located on or within or near the housing 230 of the patient sensor. In some embodiments, the gatekeeper electrical signal is produced by a signal generator comprising a temperature sensor 290, such as an ambient temperature sensor. In some embodiments, the signal generator is only an ambient temperature sensor; in some embodiments, a temperature sensor 290 is in electrical communication with a gatekeeper electrical signal generator for producing the gatekeeper electrical signal. The temperature sensor 290 can be structured, positioned, and/or oriented in a variety of different ways. For example, the temperature sensor 290 can comprise a temperature-sensitive electrical component, such as a diode or a transistor or a thermistor or another electrical component, in which the output voltage or another quality of the electrical signal or the resistivity of the component changes as a function of the temperature of the air or other material surrounding the electrical component that is in thermal communication with the temperature-sensitive electrical component.

It is expected that the critical-care patient monitoring system 100 will be used in settings in which the ambient temperature is generally about the level of a standard room temperature, such as about 70° F. or about 21° C., and/or within a standard room temperature range, such as at least about 65° F. and/or less than or equal to about 75° F. (or at least about 18° C. and/or less than or equal to about 24° C.). Other temperature ranges, including other standard room temperature ranges, within or outside of these temperature ranges can be utilized. The temperature sensor 290 can be configured to generally sense the ambient temperature in the patient's room or the ambient temperature at, near, or inside of the patient sensor 120 or the housing 230 of the patient sensor 120. In some embodiments, the gatekeeper temperature sensor 290 is positioned outside of the fluid-containing portion 190 of the patient sensor 120 and/or outside of fluid communication or direct thermal communication with the fluid in the patient sensor 120. In some embodiments, the gatekeeper temperature sensor 290 is isolated or separated from, is largely unaffected by, and/or is unable to provide clinically useful information about, changes in a patient's body temperature or other physiological parameters of a patient. In some embodiments, the gatekeeper electrical signal can help ensure that the critical-care patient monitoring system is used in an environment in which ambient temperature ranges will not affect the functioning of the electrical equipment and/or the physiological readings obtained from a patient.

In some embodiments, the gatekeeper electrical signal generator 250 is in electrical communication with the gatekeeper temperature sensor 290. The gatekeeper electrical signal generator can comprise an electrical circuit configured to produce a gatekeeper electrical signal in concert with the gatekeeper temperature sensor 290. In some embodiments, the electrical signal produced by the gatekeeper electrical signal generator 250 varies as a function of the ambient temperature sensed by the temperature sensor 290. In some embodiments, the electrical signal produced by the gatekeeper electrical signal generator 250 is a generally constant value so long as the temperature sensed by the temperature sensor 290 is within a predetermine range, such as within a predetermined range of standard room temperatures.

The gatekeeper electrical signal can be conveyed from the gatekeeper electrical signal generator 250 (located on or in the patient sensor 120, in some embodiments) to the computer monitor 110 of the critical-care patient monitoring system 100 by way of an electrical wire 165 that is separate from the electrical wire or wires 167 configured to convey the patient-information electrical signal. The electrical wires 165, 167 can be separately insulated and bound together in a common wire bundle 160. In some embodiments, the gatekeeper electrical signal is independent from the patient-information signal and does not include any information about the physiological status or condition of a patient.

In some embodiments of patient sensors, the gatekeeper electrical signal is not produced from or using an actual temperature sensor or a temperature value, but instead creates a simulated temperature signal using an electrical signal generator. In FIG. 2, the connection between the temperature sensor 290 and the gatekeeper electrical signal generator is represented by a dashed line to demonstrate that it need not exist in some embodiments because there may not be a temperature sensor 290 at all. A gatekeeper electrical signal derived from a simulated temperature is not based upon a temperature reading and may not vary at all, or may not vary appreciably, according to changes in temperature. The patient sensor 120 may not include a temperature sensor at all, at least not an ambient temperature sensor. The simulated temperature signal may be utilized in situations where the room or ambient temperature is not expected to be outside of any range that would affect the proper functioning of the electronic components or the patient's physiological condition; or where there is little or no risk of sensor misattachment or a mix-up in the type of sensor to be used; or when it is desired to produce a simpler sensor with less electronic complexity. The gatekeeper electrical signal produced with a simulated temperature signal can be configured to be generally in the same range as the signal that would ordinarily be produced and transmitted by a temperature-sensing gatekeeper or verification signal generator.

A supplier can provide a disposable patient sensor 120, or an intermediate device, such as an electrical communication wire or cable, for use with a computer monitor 110, that is configured to provide a gatekeeper signal to the computer monitor 110. The supplier can provide instructions to a healthcare provider, or other user, to electrically connect the sensor and/or the intermediate device, to a computer monitor 110 that is configured to monitor an electrical gatekeeper input port for an electrical gatekeeper signal. The sensor may or may not actually provide a gatekeeper signal that is representative of a true temperature; rather, the gatekeeper signal may be a real or simulated signal. The supplier can provide instructions to the user to remove and/or discard the sensor after use by a patient, such as in a biohazard receptacle.

The computer monitor 110 of the critical-care patient monitoring system 100 can comprise a computer processor, a computer display 280 configured to display physiological information about the patient (including one or any combination of any of the physiological information that the patient sensor is configured to obtain), a power source (such as a battery or a power cord), and one or more electrical connectors, 270, 240 configured to establish an electrical connection with the patient sensor, such as by way of an attachment with one or more electrical connectors 240 that form part of the patient sensor. The computer monitor 110 can be configured to receive one or more patient-information electrical signals that convey information about a patient's physiological conditions. One or more components of the computer monitor 110 may be releasably coupled to the other components of the monitor. For example, the display 280 may be detachable from the base. The display 280 may include the computer processor and other electrical circuitry used in processing the signals, or the processor may be included in other components of the monitor 110.

The computer monitor 110 also can be configured to receive a gatekeeper electrical signal. In some embodiments, the computer monitor 110 is configured to receive, process, calculate, and/or identify an ambient temperature value from the gatekeeper electrical signal, which can be an actual ambient temperature value or a simulated ambient temperature value.

Figure 4:
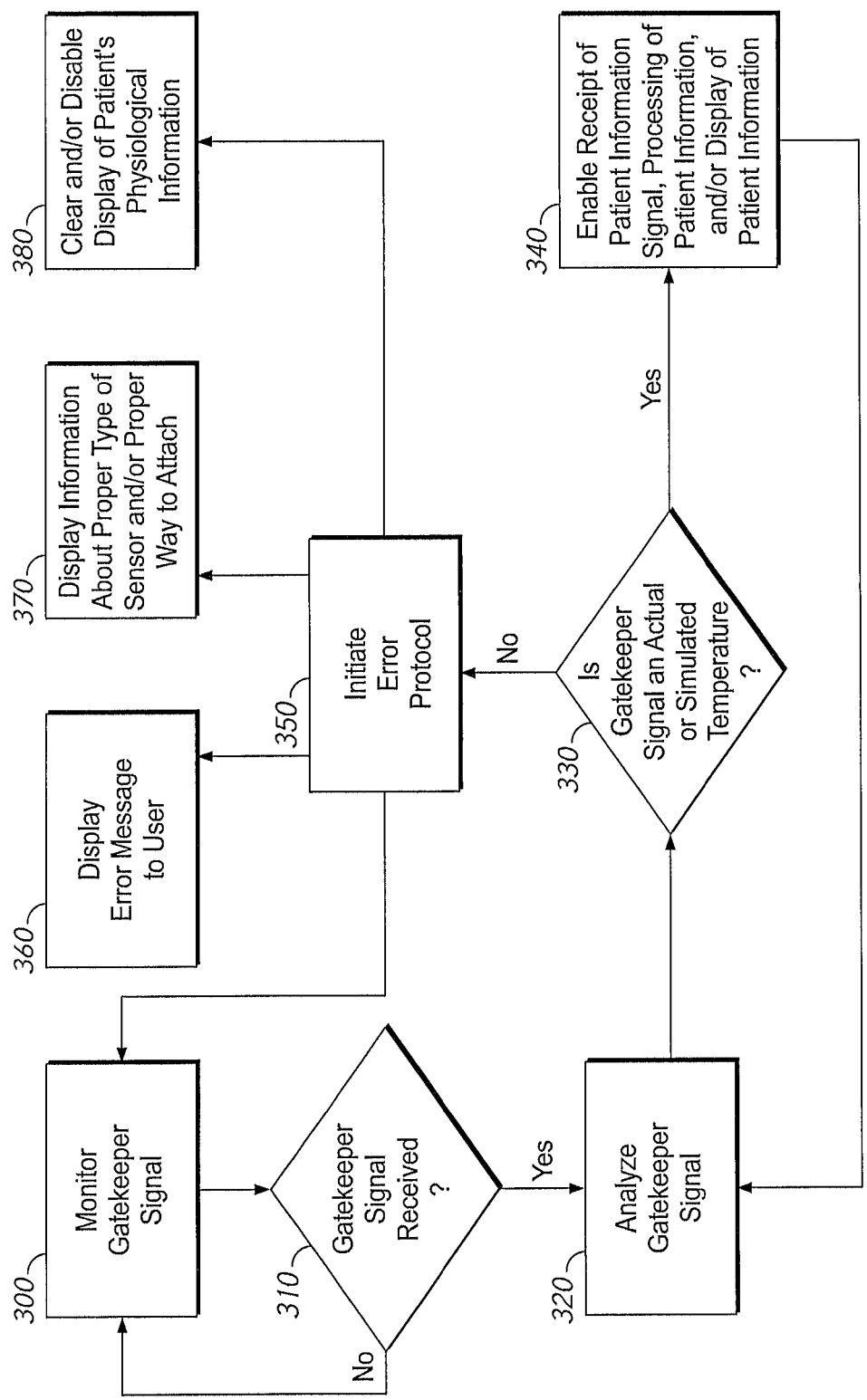
FIG. 4 illustrates an example of an algorithm or subroutine in a computer monitor for monitoring, evaluating, and/or responding to a gatekeeper electrical signal.

As schematically illustrated in an example in FIG. 4, block 300 shows that the computer monitor 110 can monitor the gatekeeper signal or verification signal, such as on a generally continuous basis, checking periodically whether a gatekeeper signal or verification signal has been received, as shown in block 310. If some type of electrical signal has been received by the monitor 110 at the gatekeeper signal electrical connection, then the computer processor of the monitor 110 can be configured to analyze the signal, as shown in block 320, to determine whether the signal is within a particular range of values, or exhibits a particular shape or variance over time, and/or demonstrates any other particular characteristics that the computer processor of the monitor 110 is programmed to recognize as indicative of a gatekeeper signal (such as either an actual temperature signal or a simulated temperature signal), as shown in block 330.

In some embodiments, as illustrated in block 340, the computer monitor 110 can be programmed to enable receipt of the patient information signal, processing of the patient information, storage of the patient information signal in memory, transmission of the patient information signal, and/or display the patient information, only after, and/or only for so long as, the gatekeeper electrical signal is transmitted to the computer monitor. In some embodiments, the computer monitor 110 receives the gatekeeper signal from the patient sensor 120 and compares it to a predetermined range of values, thus determining whether the ambient temperature sensed by the patient monitor is within a predetermined range of ambient temperatures, such as a predetermined range of standard room temperature values. As shown in block 350, if the signal received at the gatekeeper signal electrical connection on the monitor 110 is determined not to be an actual or simulated temperature signal, then the monitor 110 can initiate an error protocol, which in some embodiments can produce one or more displays of information to the user, such as an error message, as shown in block 360, or information about the proper type of sensor 120 and/or cable to be used with critical-care patient monitoring system 100, and/or the proper way to attach a sensor 120, as shown in block 370; and/or the error protocol can clear and/or disable the display of physiological information from the patient on the computer display 280, as shown in block 380, since such information might be incorrect or unreliable if the gatekeeper signal or verification signal is determined to be incorrect.

In some embodiments, the computer processor of the computer monitor does not utilize the gatekeeper electrical signal to process, analyze, calculate, or obtain any patient information from the patient-information electrical signal or signals or from any other source; rather, the patient information contained in the patient-information electrical signal is independent from and is not required to be calibrated, adjusted, or modified by the gatekeeper electrical signal.

When the gatekeeper electrical signal represents a simulated temperature value, but not an actual temperature value, the computer monitor can in some embodiments receive such gatekeeper electrical signal as an actual temperature value and proceed to function normally and display patient data in a normal manner, as though the gatekeeper electrical signal were produced using an actual temperature value. Since the gatekeeper electrical signal is not normally utilized to calibrate, modify, normalize, or adjust the patient information in the patient-information electrical signal, the simulated temperature value of the gatekeeper electrical signal may not affect the accuracy of the patient data. Thus, the same computer monitor can be configured to function properly, in some embodiments, with a patient sensor that is configured to produce a gatekeeper electrical signal using an actual temperature measurement or a patient sensor that merely produces a signal with a simulated temperature.

The invention claimed is:
1. A disposable patient-monitoring device having first and second wires and configured to be attached to tubing in fluid communication with a patient's blood vessel, and configured to be attached in electrical communication with a medical device, the patient-monitoring device comprising:

at least one pressure sensor configured to be in fluid communication with the patient's blood vessel through a fluid-receiving region in the pressure sensor and configured to be in electrical communication with the medical device using the first wire, the pressure sensor being configured to sense a pressure wave in the patient's vasculature and being configured to transmit, with the first wire, at least one patient-information electrical signal that indicates a physiological parameter of the patient to the medical device; and a temperature signal generator that is configured to send a gatekeeper electrical signal to the medical device from the disposable patient-monitoring device with the second wire, to enable the medical device to confirm that the patient-monitoring device is attached in electrical communication with the medical device, the gatekeeper electrical signal not including diagnostic or physiological information about the patient;

wherein the gatekeeper electrical signal is not configured to be used to modify the physiological parameter conveyed by the patient-information electrical signal in order for the patient-information electrical signal to indicate the physiological parameter of the patient; and wherein the temperature signal generator does not receive information from the pressure sensor.

2. The disposable patient-monitoring device of claim 1, in combination with the medical device.

3. The disposable patient-monitoring device of claim 1, further comprising a housing.

4. The disposable patient-monitoring device of claim 3, wherein the device is configured to measure an actual ambient temperature.

5. The disposable patient-monitoring device of claim 4, wherein the ambient temperature is measured inside of the housing.

6. The disposable patient-monitoring device of claim 4, wherein the ambient temperature is measured outside of the housing.

7. The disposable patient-monitoring device of claim 1, wherein the gatekeeper electrical signal is generated by a simulator, not an actual temperature measurement.

8. The disposable patient-monitoring device of claim 7, wherein the device does not include any temperature sensor.

* * * * *